(12) United States Patent
Kessler et al.

(10) Patent No.: US 11,596,750 B2
(45) Date of Patent: Mar. 7, 2023

(54) INHALER, PARTICULARLY ELECTRONIC CIGARETTE PRODUCT, AND COMPUTER PROGRAM PRODUCT

(71) Applicant: KÖRBER TECHNOLOGIES GMBH, Hamburg (DE)

(72) Inventors: Marc Kessler, Hamburg (DE); Gunnar Niebuhr, Hamburg (DE); Rene Schmidt, Buchholz I.D.N. (DE); Cameron John Wagenknecht, Hamburg (DE); Bjoern Schlueter, Bargteheide (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 264 days.

(21) Appl. No.: 16/755,713

(22) PCT Filed: Oct. 11, 2018

(86) PCT No.: PCT/EP2018/077718
§ 371 (c)(1),
(2) Date: Apr. 13, 2020

(87) PCT Pub. No.: WO2019/072960
PCT Pub. Date: Apr. 18, 2019

(65) Prior Publication Data
US 2021/0195957 A1    Jul. 1, 2021

(30) Foreign Application Priority Data
Oct. 13, 2017  (DE) .......................... 102017123867.0

(51) Int. Cl.
*A24F 47/00*     (2020.01)
*A61M 15/06*     (2006.01)
(Continued)

(52) U.S. Cl.
CPC ........... *A61M 15/06* (2013.01); *A24B 15/167* (2016.11); *A24F 40/30* (2020.01); *A24F 40/50* (2020.01);
(Continued)

(58) Field of Classification Search
CPC ................ A24F 40/30; A24F 40/46
See application file for complete search history.

(56) References Cited

U.S. PATENT DOCUMENTS 4,532,530 A    7/1985  Hawkins
5,505,214 A    4/1996  Collins et al.
(Continued)

FOREIGN PATENT DOCUMENTS

CN    202233002 U    5/2012
CN    203597405 U    5/2014
(Continued)

OTHER PUBLICATIONS

German Search Report issued by the German Patent and Trademark Office dated May 25, 2018 for German Patent Application No. 10 2017 123 867.0.
(Continued)

*Primary Examiner* — Eric Yaary
(74) *Attorney, Agent, or Firm* — Saliwanchik, Lloyd & Eisenschenk (57) ABSTRACT

The invention relates to an inhaler, particularly an electronic cigarette product, comprising at least one evaporator device having at least one electrical evaporator for evaporating liquid supplied to the evaporator and an electronic control device for controlling and/or regulating the evaporator. A plurality of liquids are associated or can be associated with the evaporator device in such a way that the composition and/or the vapour production rate of the vapour/aerosol produced by the at least one evaporator can be adjusted
(Continued)

and/or modified in a targeted manner, as the control device is designed for individual control of the at least one or each individual evaporator and/or for group control of the evaporators.

15 Claims, 6 Drawing Sheets (51) Int. Cl.
*A24F 40/30* (2020.01)
*A24F 40/50* (2020.01)
*A24B 15/167* (2020.01)
*A24F 40/10* (2020.01)
*A24F 40/20* (2020.01)
*A24F 40/60* (2020.01)
*A24F 40/65* (2020.01)

(52) U.S. Cl.
CPC .............. *A24F 40/10* (2020.01); *A24F 40/20* (2020.01); *A24F 40/60* (2020.01); *A24F 40/65* (2020.01)

(56) References Cited

U.S. PATENT DOCUMENTS

| | | |
|---|---|---|
| 2006/0196968 A1 | 9/2006 | Rabin et al. |
| 2013/0192620 A1* | 8/2013 | Tucker ................. H05B 1/0244 131/329 |
| 2014/0060554 A1 | 3/2014 | Collett et al. |
| 2014/0366898 A1 | 6/2014 | Monsees |
| 2015/0090280 A1 | 4/2015 | Chen |
| 2016/0089508 A1 | 3/2016 | Smith |
| 2016/0219938 A1 | 8/2016 | Mamoun et al. |
| 2016/0262454 A1 | 9/2016 | Sears et al. |
| 2016/0338407 A1 | 11/2016 | Kerdemelidis |
| 2016/0345630 A1 | 12/2016 | Mironov et al. |
| 2017/0042230 A1 | 2/2017 | Cameron |
| 2017/0150755 A1 | 6/2017 | Batista |
| 2017/0188626 A1 | 7/2017 | Davis et al. |
| 2017/0251721 A1 | 9/2017 | Rostami et al. |
| 2017/0251727 A1 | 9/2017 | Nielsen |
| 2017/0258132 A1 | 9/2017 | Rostami et al. |
| 2017/0258140 A1 | 9/2017 | Rostami et al. |
| 2018/0289908 A1* | 10/2018 | Marmur ............... A61M 11/001 |
| 2018/0343922 A1* | 12/2018 | Stadler ................. A24F 40/485 |
| 2019/0124982 A1* | 5/2019 | Atkins .................. A24F 40/30 |
| 2019/0217028 A1* | 7/2019 | Nakano ................ A24F 40/485 |
| 2019/0246696 A1 | 8/2019 | Schmidt et al. |
| 2020/0205478 A1 | 7/2020 | Dick et al. |

FOREIGN PATENT DOCUMENTS

| | | |
|---|---|---|
| DE | 10 2015 107 082 A1 | 5/2015 |
| DE | 10 2016 002 665 A1 | 3/2016 |
| EP | 2 989 912 A1 | 3/2016 |
| EP | 3 170 413 A1 | 5/2017 |
| GB | 2 524 779 A | 10/2015 |
| WO | WO 2014/066730 A1 | 2/2014 |
| WO | WO 2015/038981 A2 | 3/2015 |
| WO | WO 2015/076515 A1 | 5/2015 |
| WO | WO 2016/090426 A1 | 6/2016 |
| WO | WO 2017/009002 A1 | 1/2017 |
| WO | WO 2017/048782 A1 | 3/2017 |
| WO | WO 2017/153270 A1 | 9/2017 |
| WO | WO 2017/167509 A1 | 10/2017 |
| WO | WO 2017/175218 A2 | 10/2017 |
| WO | WO 2018/083007 A1 | 5/2018 |

OTHER PUBLICATIONS

Examination Report issued by the Japanese Patent Office dated Oct. 25, 2022 for parallel Japanese patent application No. 2020-520627.
Opposition issued by G.D S.p.A. dated Dec. 1, 2022 for parallel European patent application No. 18785944.2.
Office Action issued by Chinese Patent Office dated Nov. 22, 2022 for parallel Chinese patent application No. 201880066413.6.

* cited by examiner

INHALER, PARTICULARLY ELECTRONIC CIGARETTE PRODUCT, AND COMPUTER PROGRAM PRODUCT

CROSS REFERENCE TO RELATED APPLICATIONS

This application is a National Stage Application of International Application Number PCT/EP2018/077718, filed Oct. 11, 2018; which claims priority to German Patent Application No. 10 2017 123 867.0, filed Oct. 13, 2017.

The present invention relates to an inhaler, particularly an electronic cigarette product, comprising at least one evaporator device having at least one electrical evaporator for evaporating liquid supplied to the evaporator and an electronic control device for controlling and/or regulating the evaporator. The invention further relates to a computer program product, particularly an application software or app, for a mobile communication terminal, for controlling and/or adjusting such an inhaler.

Current electronic cigarettes use between one and up to five evaporator heads based on the wick-spiral principle, which draw their liquid from a common reservoir. The consumer can only adjust the total output of the evaporation device and thereby the amount of vapour produced; further adjustments are not possible.

The object of the invention is to provide an inhaler having a variety of adjustment options, which allows for high added value for the consumer due to a high degree of customisation of the smoking experience in terms of amount of vapour and taste.

The invention achieves said object by means of the features of the independent claims. According to the invention, a plurality of liquids are associated or can be associated with the evaporator device in such a way that the composition and/or the vapour production rate of the vapour/aerosol produced by the at least one evaporator can be adjusted and/or modified in a targeted manner, as the control device is designed for individual control of the at least one or each individual evaporator and/or for group control of the evaporators. Due to the individual control of the at least one evaporator, it is possible to adjust and/or modify the amount of vapour and/or the composition of the vapour/aerosol produced by the at least one evaporator in a targeted manner by supplying the same or different liquids, as a result of which the smoking experience can be individually adjusted by the consumer.

The allocation according to the invention of the plurality of liquids to the at least one evaporator can advantageously be implemented by means of a plurality of liquid feeds for supplying the plurality of liquids to the at least one evaporator.

The invention comprises the possibility of influencing the vapour quality with only one evaporator, for example via a suitable frequency control of the evaporator.

A plurality of parameter sets adapted to the different liquids are preferably stored in the electronic control device. This makes it possible to evaporate the liquids or the liquid mixture optimally with regard to the desired effect and/or the desired taste experience.

In advantageous embodiments of the invention, the evaporator device has a plurality of evaporators. This makes it possible to evaporate the same and/or different liquids with one or more evaporators that are optimally adapted to the respective liquid. In addition, due to an advantageous individual controllability of individual evaporators with possibly different heating parameters, there is greater variability in the evaporation process. Accordingly, at least one separate evaporator is advantageously associated with each liquid.

A plurality of evaporators for a liquid can advantageously multiply or increase the vapour volume and/or enhance the performance of the evaporator device. Accordingly, a plurality of evaporators can be provided for evaporating the same liquid in order to increase the evaporation capacity with regard to a specific liquid. Several evaporators can also be provided for several or all the liquids in order to increase the evaporation capacity for the respective liquids. The number of evaporators is basically independent of the connection to the liquid reservoirs. Increasing the number of evaporators for a liquid is advantageous compared to increasing the size of the evaporator itself.

The inhaler advantageously has a user interface via which a user, particularly the consumer, can influence the composition of the vapour or aerosol produced by the at least one evaporator. The user interface is particularly advantageously a wireless interface, for example a Bluetooth interface, for communication with a user's mobile communication terminal, particularly a smartphone. In this way, the inhaler can be easily adjusted as desired.

An advantageous application of the invention relates to an electronic cigarette product, in short an e-cigarette. In this case, the liquids contain the same and/or different proportions or mixing ratios of 1,2-propylene glycol, glycerol, water, at least one active ingredient, particularly nicotine, and/or at least one flavouring agent (flavour).

Preferably at least one of the liquids contains more than 50% glycerol, which is a good vapour generator.

Furthermore, at least one of the liquids contains at least 1% nicotine and at least one of the liquids contains no nicotine. This allows a high variability of the nicotine content in the vapour/aerosol.

Within the scope of this application, percentages for liquid fractions can generally be percentages by volume and/or weight.

In one embodiment, each of the liquids supplied to the at least one evaporator is free of nicotine in order to allow the production of a nicotine-free vapour/aerosol and/or to avoid excessive heating of nicotine.

Furthermore, at least one of the liquids contains a flavour and at least one of the liquids contains no flavour, or another flavour. This allows a high variability in the content of one or more flavours in the vapour or aerosol.

The inhaler advantageously has a plurality of liquid stores or reservoirs for storing the multiple liquids. By using one or more liquid stores, which can advantageously be individually assigned to one or more evaporators and/or one or more evaporator carriers, individual evaporators and/or evaporator carriers can evaporate the same liquids and/or different liquids with different compositions.

Advantageously, at least one of the liquids mostly contains one or more components from the group 1,2-propylene glycol and another of the liquids mostly contains glycerol. Liquids having different mixing ratios can then be provided in several reservoirs, so that the ratio of the flavour and/or active ingredients can be adjusted and/or modified in a vapour mixture produced during the evaporation. The ratio of the flavour and/or active ingredients of the vapour mixture can advantageously be adjusted continuously.

For this purpose, different mixing ratios of one or more components from the group 1,2-propylene glycol and glycerol can be present in the two liquids. In one embodiment, the ratio of the proportions of one or more components from the group 1,2-propylene glycol and glycerol in one liquid is greater than 50/50 and in the other liquid is less than 50/50;

the ratio of the proportions in one liquid is advantageously greater than 75/25 and in the other liquid less than 25/75, for example the ratio of the proportions in one liquid is 90/10 and in the other liquid 10/90. The ratio of the proportions may refer to the ratio of the mass proportions, substance quantity proportions, and/or volume proportions.

In one embodiment, the inhaler has at least one capsule for storing a solid containing flavour ingredient(s) and/or active ingredient(s), particularly containing nicotine. The vapour/aerosol produced by the at least one evaporator can preferably flow through the capsule in order to avoid overheating of the nicotine. In this embodiment, the capsule is preferably arranged or positioned downstream of the evaporator. The vapour or aerosol produced by the evaporator flows through the capsule, wherein the nicotine is released by the vapour/aerosol from the nicotine-containing solid and is transported to the mouthpiece. In particular, the nicotine-free liquid is evaporated and flows through the capsule with processed tobacco and/or nicotine for preparing the vapour/aerosol before it is consumed by the consumer. The ratio between one or more components from the group 1,2-propylene glycol and glycerol of the vapour/aerosol can be important for the taste development.

The solid can be a tobacco-containing material, for example nicotine-containing granules and/or beads. In this embodiment, there is advantageously no nicotine in any of the liquids supplied to the evaporator. In this embodiment, the inhaler is a hybrid system which is designed to evaporate a liquid and to release nicotine from a solid.

The invention further provides a computer program product, particularly an application software or app, for a mobile communication terminal, in particular a smartphone. The computer program product is designed to control and/or adjust the inhaler, particularly via a wireless interface, for example a Bluetooth interface. Communication terminals such as smartphones have such a wireless interface and allow an intuitive and detailed control and/or adjustment of the inhaler, as well as the display of information relating to the inhaler, on a generally touch-sensitive screen via a graphical user interface.

The computer program product preferably has selection elements for selecting one of a plurality of preset evaporation profiles, and for corresponding actuation of the inhaler. For example, an evaporation profile with little active ingredient and/or low throat hit, an evaporation profile with high active ingredient and/or high throat hit, and possibly an intermediate evaporation profile therebetween can be provided. Of course, more than three different evaporation profiles can be provided. In general, preset evaporation profiles can be provided for adjusting at least two, preferably at least three different degrees of strength in terms of active ingredient content and/or throat hit.

A relatively small number of preset evaporation profiles are preferred by consumers who want to adjust a few different smoking experiences quickly and easily and do not need highly differentiated adjustment options.

The computer program product, particularly the application software or the graphical user interface thereof, preferably comprises adjustment elements for adjusting individual evaporation parameters of the inhaler. This manual mode is aimed at consumers who want a high degree of differentiated adjustment options.

In this mode, the computer program product, particularly the application software or the graphical user interface thereof, advantageously comprises adjustment elements for adjusting the proportion of individual liquids in the vapour/aerosol produced; an adjustment element for adjusting a throat hit; and/or an adjustment element for adjusting the total amount of vapour produced.

The computer program product, particularly the application software or the graphical user interface thereof, advantageously comprises an adjustment element for adjusting the flavour and/or active ingredient content in order to allow consumers to easily adjust the flavour and/or active ingredient content. For example, the mixing ratio of a vapour mixture of one or more components from the group 1,2-propylene glycol and glycerol can be adjusted by the adjustment element.

A higher proportion of glycerol leads to more vapour development. A higher proportion of one or more components from the group 1,2-propylene glycol leads to a stronger effect in the throat or throat hit. The mixing ratio of the vapour mixture can in particular be individually adjusted and/or modified by the consumer to a mixture that is pleasant to the consumer while the cartridge is being consumed.

In one embodiment, nicotine can be added to the vapour mixture. The addition of nicotine is possible through one/the adjustment element. The degree of saturation of the vapour mixture with nicotine can advantageously be modified and/or adjusted by the mixing ratio. The evaporation behaviour of the flavour and/or active ingredients, particularly nicotine, can thus be adjusted over time, and the course of time of the individual taste experience and administration of the active ingredient can thus be influenced.

In one embodiment, the nicotine is in a capsule storing nicotine-containing solids. The adjustment element can influence the flow through the capsule, particularly the speed and temperature of air that is flowing through, and thus the release of nicotine and the addition of nicotine into the air flow or into the vapour/aerosol.

The selectability and/or adjustability of the evaporation parameters is coupled to one another. The computer program product takes into account all interdependencies of the evaporation parameters and adjusts the visual representation in the graphical user interface accordingly.

To inform the consumer, an indication of the state of charge of the energy store in the inhaler and/or an indication of the remaining amount of liquid in the reservoir(s) of the inhaler, and/or an indication of the puffs remaining to the consumer is also advantageously provided. The number of remaining puffs can be calculated depending on the selected adjustments, the smoking behaviour, for example the average individual puff durations, and the energy requirement.

The computer program product can preferably have a switching element for adjusting the puff resistance of the inhaler, which provides the consumer with a further variability in the smoking experience. For example, the switching element can be used to adjust a puff resistance corresponding to a conventional cigarette and/or the lowest possible puff resistance.

The invention will be explained below on the basis of the preferred embodiments with reference to the accompanying drawings. In the drawings.

Figure 1:
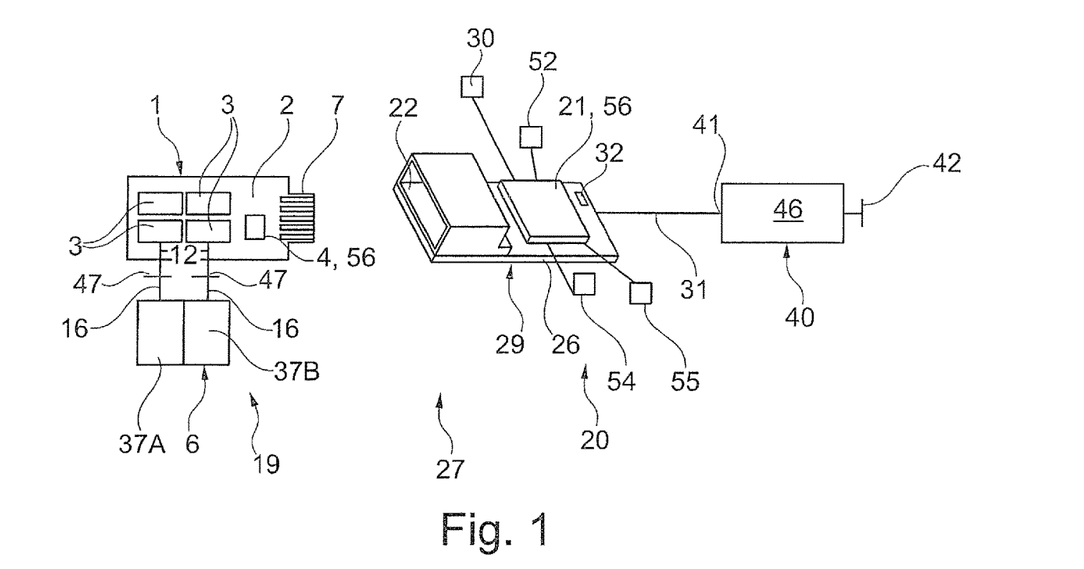
FIG. 1 is a schematic representation of an e-cigarette in one embodiment of the invention.

The component system for an inhaler 27 shown by way of example in FIG. 1 comprises an evaporator device 1 and an advantageously reusable base part 20.

The evaporator device 1 comprises at least one carrier 2, which can also be referred to as a carrier plate, and at least one liquid store 6 to be connected or that is connected to the carrier 2. Each carrier 2 has at least one evaporator 3, which serves to evaporate liquid supplied to the evaporator 3 from the at least one liquid store 6. The liquid supplied to the evaporator 3 is thus converted into vapour/aerosol by the evaporator 3. The in particular electrical evaporator 3 has at least one, preferably a plurality of electrical resistance heating elements. The evaporator 3 is preferably arranged in relation to an upper side of the carrier 2, so that vapour and/or aerosol produced by the evaporator 3 emerges from the upper side of the carrier 2.

The evaporator device 1 is advantageously formed from one or more structural units or evaporator units 19, each consisting of at least one carrier 2, each having at least one evaporator 3 and in each case at least one liquid store 6. The evaporator units 19 are advantageously exchangeable cartridges.

A digital electronic control device 4, for example an application-specific integrated circuit (ASIC), is advantageously arranged on the carrier 2. The evaporators 3 can be controlled individually or in groups by the electronic control device 4 and heated by electricity from an energy store 46 in order to evaporate any liquid present on the heating elements.

The carrier 2 has an electrical connector part 7, here in the form of an electrical plug, having a plurality of electrical contacts 10. The contacts 10 are connected to the electronic control device 4 by means of electrical lines in order to transmit sensor signals, control signals and/or electrical energy between the base part 20 and the evaporator unit 19. The advantageously continuous, dimensionally stable carrier 2 can consist of a suitable, advantageously non-conductive material, for example ceramic or a suitable plastics material, particularly PEEK, or fibre-reinforced plastic, for example PCB material. Sensors, for example temperature sensors for measuring the heating temperature and/or a pressure sensor for measuring the flow pressure, can be provided on the evaporator device 1.

The base part 20 comprises a control unit 29 and an energy storage unit 40 connected or to be connected to the control unit 29. The control unit 29 comprises an electronic controller 21 and an electrical socket 22 electrically connected to the electronic controller 21. The electronic controller 21 and the electrical socket 22 are advantageously arranged on a common circuit board 26. The entirety of electronic control device 4 and electronic controller 21 is referred to in the context of this application as an electronic control device 56 of the inhaler 27.

The electrical plug 7 and the electrical socket 22 are set up correspondingly with respect to one another, so that by plugging the plug 7 into the socket 22 an electrical connection is established between the evaporator device 1 and the base part 20 for the transmission of signals, data and/or electrical power. In the evaporator device 1, the supply currents and signals from the plug 7 are forwarded to the at least one evaporator 3 and/or to sensors. The plug 7 and the socket 22 advantageously each have the same number of electrical contacts 10. To connect the evaporator device 1 to the base part 20, the evaporator device 1 is pushed into the base part 20 parallel to the longitudinal axis thereof, possibly also via an adapter or an extension part, whereby the plug 7 is pushed into the socket 22 and the electrical connection is established.

An identifier or ID (identification information) of the evaporator device 1 is advantageously permanently stored in the electronic control device 4 of the evaporator device 1. As a result of connecting an evaporator device 1 to a base part 20 by inserting the plug 5 into the socket 22, the electronic controller 21 can read the identifier from the control device 4 and carry out or initiate type-specific individual control of the respective evaporator 3 on the evaporator device 1, for example by transmission of control and/or regulation commands to the control device 4.

Control data for a plurality of identifiers corresponding to a plurality of different evaporators or evaporator types and/or liquids are preferably stored in the electronic controller 21 of the base part 20, for example in the form of a database. When the electronic controller 21 reads an identifier from the memory 14 of the evaporator device 1, it can call up the control data associated with this identifier from the database and carry out the control of the evaporator 3 according to the type and adapted to the liquid to be evaporated.

The energy storage unit 40 comprises an energy store 46, a battery interface 41 for connecting the control unit 29 to the energy storage unit 40 via electrical lines 31, and a charging interface 42. The control unit 29 is supplied with current via the battery interface 41. Furthermore, analogue and/or digital signals can be transmitted between the energy storage unit 40 and the control unit 29 via the battery interface 41. In an advantageous embodiment, the electrical lines 31 comprise a digital data bus. The electrical connection 31 between the base part 20 and the energy storage unit 40 can be used, for example, to transmit information about the state of charge of the energy store 46 or diagnostic data between the control unit 29 and the energy storage unit 40.

The energy store 46 can be a disposable battery or a rechargeable battery, for example a lithium-ion battery. In the embodiment shown, the energy store 46 is a rechargeable battery which can be charged via the charging interface 42, for example a USB interface.

Each evaporator unit 19 advantageously has a standardised liquid interface 47 for connecting the at least one liquid store or liquid tank 6 to the carrier 2. The liquid interface 47 is advantageously arranged on the underside or on the side of the carrier 2 opposite the evaporator 3. Accordingly, the liquid from the reservoir(s) 37A, 37B is provided at the liquid interface 47 and is passed through an advantageous passage opening through the carrier 2 to the evaporator(s). The liquid interface 47 can be sealed, for example, by means of a sealing element.

The connection between the at least one liquid store 6 and the carrier 2 is advantageously reversible in order to allow the user to replace the liquid store(s) 6. The at least one liquid store 6 can be designed to be refillable (reusable part) or as a disposable part. The carrier 2 and the liquid store 6 can form a unit that the consumer cannot separate and they can be designed as a disposable or reusable part.

Each liquid store 6 is connected to one or more evaporators 3 via an associated liquid feed 16 in order to transport liquid from an opening in the liquid tank 6 to the evaporator(s) 3, where it is evaporated. A capillary element 12 is advantageously provided beneath each evaporator 3, or between each evaporator 3 and the liquid store 6, i.e. in the liquid feed 16 and, for example, in a passage opening of the carrier 2, and conveys liquid from the liquid store 6 by means of capillary action, for example with the aid of microchannels, to the evaporator 3 in order to ensure the wetting of the evaporator 3 and the continuous replenishment of liquid. The capillary element 12 can comprise, for example, a pore element with an optimised pore size, an open-pore foamed element, a sponge element and/or a lamellar structure.

On the side of the carrier 2 opposite the liquid interface 47, the evaporated liquid in the form of vapour and/or aerosol is discharged via an air stream in order to be inhaled by the consumer.

The present concept accordingly provides for the use of one or more evaporators 3 on one or more, advantageously ceramic carriers or carriers 2 consisting of a temperature-resistant polymer such as PEEK. Each carrier 2 has a standardised interface 7 for electrical contacting of the evaporator(s) 3. One evaporator 3 (see FIGS. 2 and 4 to 7) or also a plurality of evaporators 3 (see FIGS. 1 and 3) can be integrated on a carrier 2 in each case.

In the embodiment according to FIG. 1, the evaporators 3 are arranged, for example, in matrix form, here for example four evaporators 3 in 2×2 matrix form.

Figure 2:
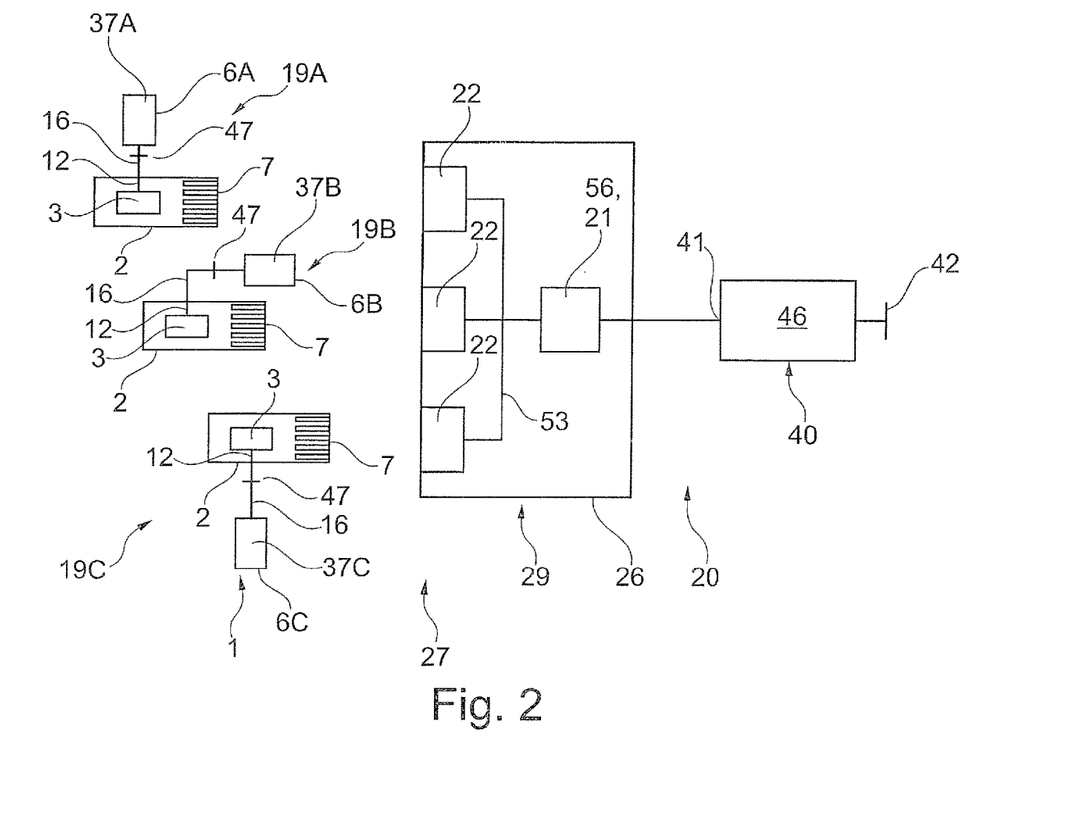
FIG. 2 is a schematic representation of an e-cigarette in a further embodiment of the invention.

The component system for an e-cigarette 27 in FIG. 2 shows the possibility of integrating, for example, three cartridges 19, each with a carrier 2 and, for example, one evaporator 3 on each carrier 2. Each carrier 2 thus contains an evaporator 3, each with its own tank 6A, 6B, 6C. With this system, three different liquids A, B, C can be released into vapour at different proportions that can be individually adjusted by the consumer and/or switched in succession.

In this embodiment and advantageously in general, the base part 20 or the control unit 29 has a number of plug connector parts 22, here plug sockets, corresponding to the number of cartridges 19, in order to allow the individual exchange of single cartridges 19. The sockets 22 are connected to the electronic controller 21 of the base part 20 via a distributor 53.

Figure 3:
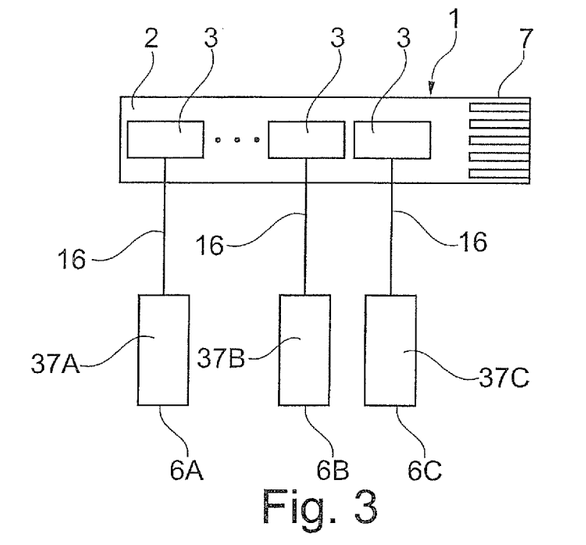
FIGS. 3-10 are schematic representations of different evaporator concepts for an e-cigarette.
Figure 4:
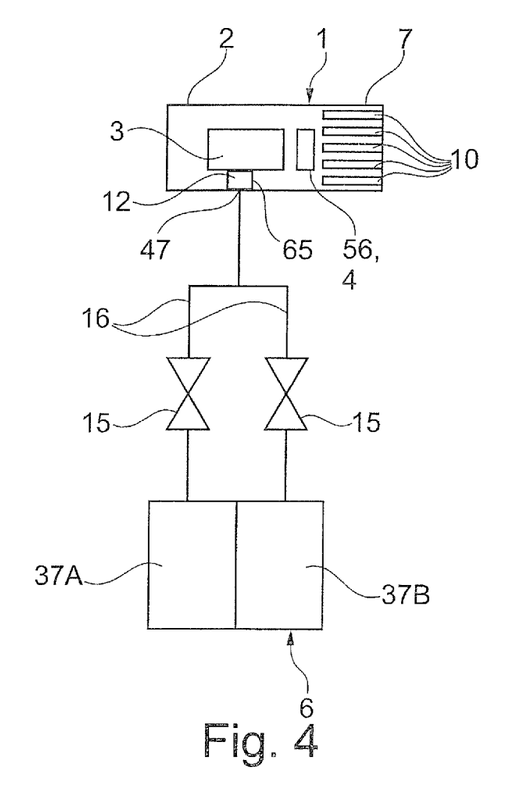

In the embodiment according to FIG. 3, the evaporators 3 are arranged in a row, for example. Other arrangements of a plurality of evaporators 3 on a carrier 2 are possible.

In the embodiments according to FIGS. 1 to 3, each reservoir 37A, 37B, . . . is assigned at least one evaporator 3, which is supplied with liquid exclusively by the assigned reservoir 37A, 37B, . . . . This has the advantage that evaporators 3 optimised for the respective liquid A, B, C can be used. In the embodiment according to FIG. 1, each reservoir 37A, 37B, . . . , for example, is assigned two evaporators 3. The vapour volume or the evaporation capacity can be increased for each reservoir 37A, 37B, . . . by increasing the number of evaporators 3, here for example by more than two evaporators 3 per reservoir 37A, 37B, . . . .

However, it is not excluded that the same evaporator 3 is supplied with liquid from a plurality of reservoirs 37A, 37B, . . . so that the same evaporator 3 is assigned to the plurality of reservoirs 37A, 37B, . . . . A corresponding embodiment is shown by way of example in FIG. 4 for two reservoirs 37A, 37B. In this case, advantageously controllable valves 15, particularly metering valves, or other elements for individually controlling/regulating the flow through the feeds 16 are provided in the feeds 16 of the plurality of reservoirs 37A, 37B in order to be able to adjust and modify the vapour composition of the evaporator 3 accordingly.

Figure 5:
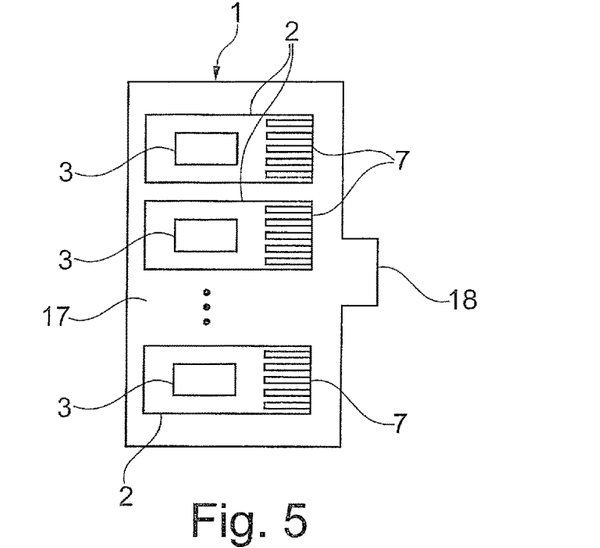
Figure 6:
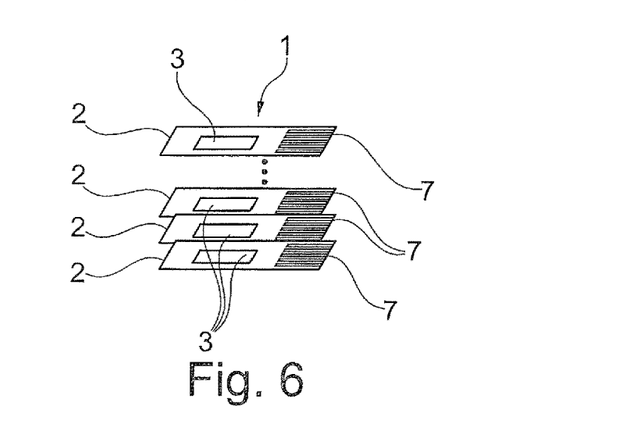
Figure 7:
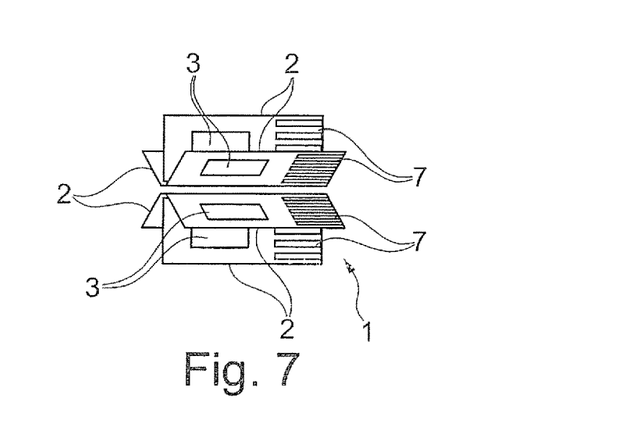

In further embodiments, the evaporator device 1 can have a plurality of carriers 2, each having one or more evaporators 3, see FIGS. 5 to 7. The plurality of carriers 2 can advantageously be combined to form a larger evaporator assembly (complex). In the embodiment in FIG. 5, a plurality of carriers 2 are arranged on a main carrier 17, here in a row, for example, and are electrically and mechanically connected thereto. The main carrier 17 can advantageously have a connector part 18 for cooperation with the connector part 22 of the base part 20. The connector part 18 is advantageously electrically connected to the connector parts 7 of the individual carriers 2. On the main carrier 17, connector parts (not shown) can be provided for cooperation with the connector parts 7 of the individual carriers 2.

In the embodiment in FIG. 6, a plurality of carriers 2 are arranged in the form of a stack, i.e. one above the other in parallel and spaced apart from one another.

In the embodiment in FIG. 7, a plurality of, for example, six carriers 2 are arranged in a star shape with the same angular spacing from one another, which can be advantageous in the case of cylindrical geometry or rod geometry of the evaporator device 1 or of the inhaler 27.

The geometries shown in FIGS. 1 to 7 for the arrangement of the evaporators 3 and the carriers 2 are to be understood as examples; the implementation of the invention is not limited to the examples shown.

The evaporator(s) 3 on the carrier(s) 2 is/are controllable as a complex, individually or in portions, i.e. in any selection. Due to their standardised interface 7, the carriers 2 are individually exchangeable within a complex. Each carrier 2 within a complex and/or each evaporator 3 of a carrier 2 can be individually electrically controlled, which allows for differentiated control of the evaporation.

The evaporation device 1 has overall a plurality of liquid reservoirs 37A, 37B, . . . that contain differently composed liquids, and a plurality of corresponding fluid inlets 16 of the reservoir 37A, 37B, . . . to the one or more evaporators 3. The liquids in the reservoirs 37A, 37B, . . . advantageously comprise one or more components, the components comprising 1,2-propylene glycol, glycerol, water, at least one active ingredient, particularly nicotine, and/or at least one flavouring agent (flavour) in different mixing ratios.

The reservoirs 37A, 37B, . . . are advantageously formed in one or more liquid stores 6. In particular, a multi-chamber tank 6 can be provided to form a plurality of reservoirs 37A, 37B, . . . . As an example, a two-chamber tank 6 is provided in each case in FIGS. 1 and 4 to form two reservoirs 37A, 37B. Of course, a liquid tank 6 can also comprise more than two reservoirs 37A, 37B.

The component system for the e-cigarette 27 in FIG. 1 shows an evaporator cartridge 19 having four evaporators 3 on a carrier 2. The carrier 2 is coupled to a tank 6 having two separate chambers, so that in each case two evaporators 3 are assigned to a reservoir 37A and 37B.

In the embodiments according to FIGS. 2 and 3, the reservoirs 37A, 37B, 37C are realised by means of single-chamber tanks 6A, 6B, 6C. That is, each tank 6A, 6B, 6C has only one chamber for forming a reservoir 37A, 37B, 37C.

Mixed forms between single and multi-chamber tanks are possible, for example a two-chamber tank and a single-chamber tank could be provided in FIG. 2 or FIG. 3.

By using several reservoirs 37A, 37B, . . . and a plurality of corresponding liquid feeds 16, the evaporator(s) 3 can evaporate different liquids contained in the reservoirs 37A, 37B, . . . and having different compositions. In this way, the composition of the vapour or aerosol produced by the evaporator(s) 3 can be adjusted in a targeted manner. Furthermore, the vapour/aerosol composition can be modified in a targeted manner by targeted evaporation of different liquids.

A plurality of liquids of the same composition can also optionally be provided in the inhaler according to the invention, for example two liquids having the same composition and one liquid having a different composition. This also results in an individualised composition of the vapour, which can be decided by the user who inserts liquid reservoirs 37A, 37B . . . into the inhaler, particularly an electronic cigarette product. In the case of an inhaler for medical applications, this can be done, for example, according to the prescription of a doctor.

The control of the evaporator(s) 3 and thus the evaporation can advantageously be done with different parameters adapted at least in part to the respective liquid.

In an exemplary implementation, one to four evaporators 3 can in each case be integrated on a carrier 2. Each evaporator 3 can have an individual control and an individual liquid supply 16. It is thus possible to use up to four different liquids per inhaler 27.

In the embodiment according to FIG. 1, for example, four evaporators 3 are integrated on a carrier 2. Here, two evaporators 3 in each case are assigned to a reservoir 37A, 37B, for example.

An exemplary implementation of the invention is explained below with reference to FIGS. 8 to 10. Two liquids A, B (FIG. 8, 9) or three liquids A, B, C (FIG. 10) are shown, but this is not a limitation.

By way of example, liquid A can have a neutral taste without flavour and can consist to a considerable or predominant extent, for example at least 50%, preferably at least 60%, particularly at least 70%, of glycerol. Liquid B can have a neutral taste or a flavour B and at the same time contain nicotine. Liquid C advantageously contains no nicotine, but a flavour C, which may differ from flavour B.

The individual liquids as components of the resulting vapour have the following roles. It is the role of the proportion of liquid A in the vapour to ensure an adjustable sudden effect in the throat of the consumer (so-called throat hit) and/or an additional amount of vapour per puff. The role of the proportion of liquid B in the vapour is to provide an adjustable amount of nicotine per puff. The role of the proportion of liquid C and, if applicable, of liquid B in the vapour is to ensure an adjustable taste development per puff. Due to the individual controllability of the evaporator 3 by the consumer, the resulting amount of vapour, amount of active ingredient, and/or flavour combination can be adjusted flexibly, i.e. the user can determine what proportion of the resulting vapour the liquids A, B and C should each make up.

The power of the individual evaporators 3 is advantageously set via pulse width modulation and regulated, for example, by measuring the current and/or the voltage and maintaining a liquid-dependent setpoint. Individual evaporators 3 are preferably utilised to a maximum of 80% in order to obtain a reserve for, for example, a short-term power boost that can be triggered by the consumer. To trigger the power boost, the housing of the inhaler 27 or of the base part 20 advantageously has a boost switch 30 which can be actuated by the consumer and is electrically connected to the electronic controller 21.

Figure 8:
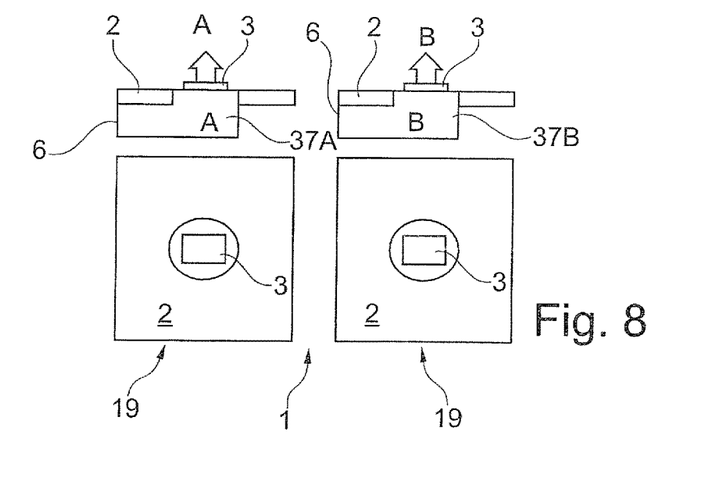

FIG. 8 shows an evaporator device 1 having two cartridges 19, each of which has a single-chamber tank 6 for the liquids A, B. FIG. 9 shows an evaporator device 1 having one cartridge 19 which has a two-chamber tank 6 for the liquids A, B. The evaporator device 1 in FIG. 1 thus corresponds to the liquid variance in FIGS. 8 and 9.

Figure 9:
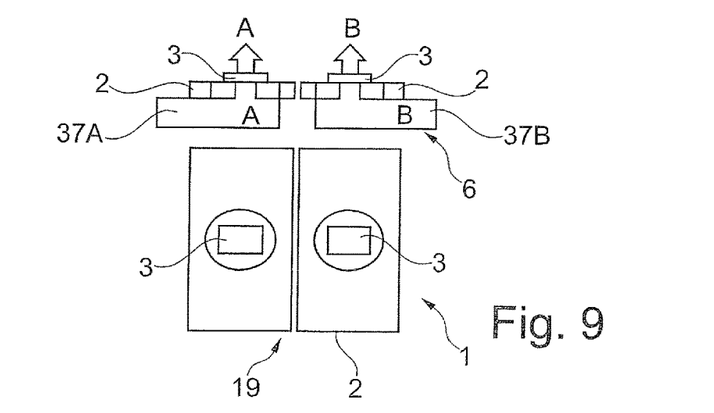
Figure 10:
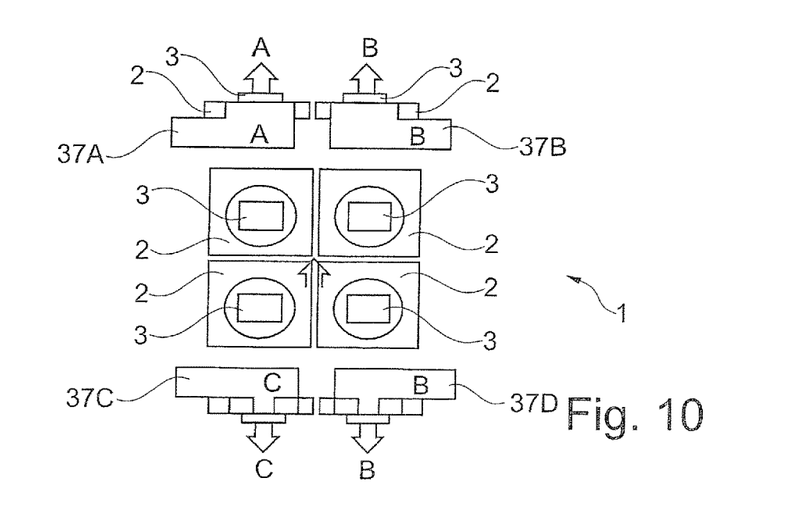

It can be seen that the evaporator device 1 in FIG. 10 can produce twice the amount of vapour as that in FIG. 8 or 9. Such an increased amount of vapour can advantageously be produced via a boost actuator 30, see FIG. 1. In controlled operation, the maximum amount of vapour can correspond to the 80% limit of the evaporator device 1 from FIG. 8. Any combination of liquids A, B, C can be achieved very flexibly and the taste and effect experience can be individually adjusted by the consumer. If a consumer prefers vapour with more or less nicotine or wants to combine different flavours, this is achieved by using the corresponding evaporator units 19 and their connected tanks 6 with the preferred liquid.

The evaporator device 1 presented in FIG. 10 could be implemented both by the arrangement in FIGS. 1 and 3 and by the arrangement in FIGS. 5 to 7. Due to the standardised interface 7, 18, the evaporator units 19 offer the advantage of allowing any combination.

The electronic control device 4 and the control of the evaporators 3 are preferably programmed specifically for each liquid A, B, C located in the liquid store 6 in order to achieve an optimal flavour and/or active ingredient administration.

In order to make the complex combinability available to the end customer, the evaporators 3 must be controlled individually. This is ensured by using a control device 4, for example an ASIC. Via the interface 7, 22, a controller 21, for example a microcontroller, sends control commands to the control device 4, said commands controlling which evaporator 3 is operated with which duty cycle and with which frequency for which period of time. In addition to the adjustable proportions of the individual evaporators 3 or liquids A, B, . . . on the vapour, the individual evaporators 3 can also be adjusted with regard to the actuation frequency and thus contribute to the total aerosol with different droplet sizes. This affects the vapour density, the throat hit and the effectiveness.

Preset evaporation profiles are preferably stored in the controller 21, which can be adapted by a wireless interface 32 and by means of an application software, or app for short, on the consumer's smartphone 33. More precisely, the smartphone 33 has a touch-sensitive screen 34. The app comprises a graphical user interface GUI, which comprises a plurality of graphical screen representations, two of which are shown by way of example in FIGS. 11 and 12.

Figure 11:
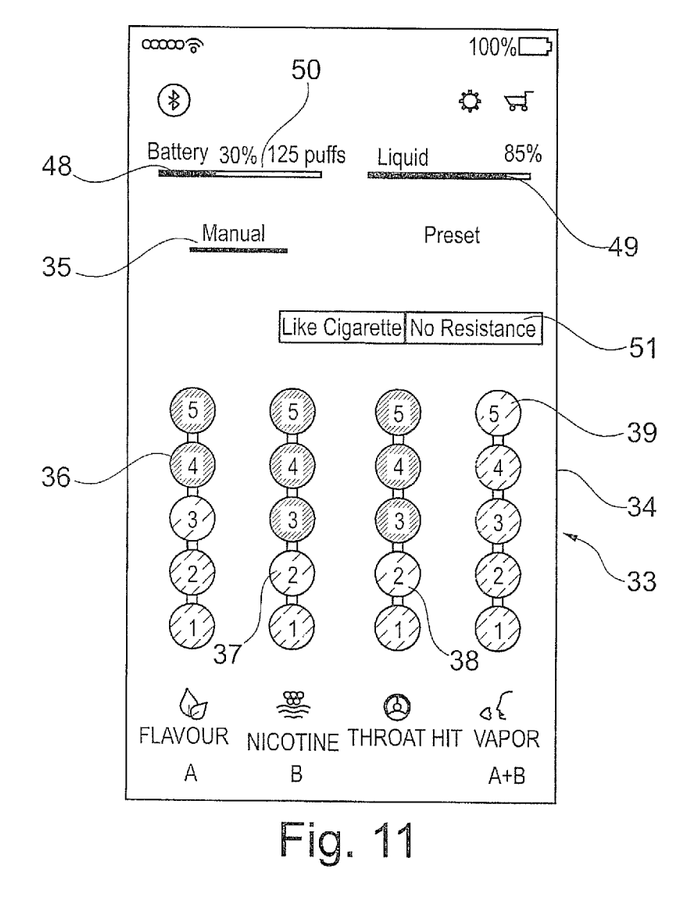
FIG. 11, 12 show screen representations of a smartphone app for operating and adjusting an e-cigarette.
Figure 12:
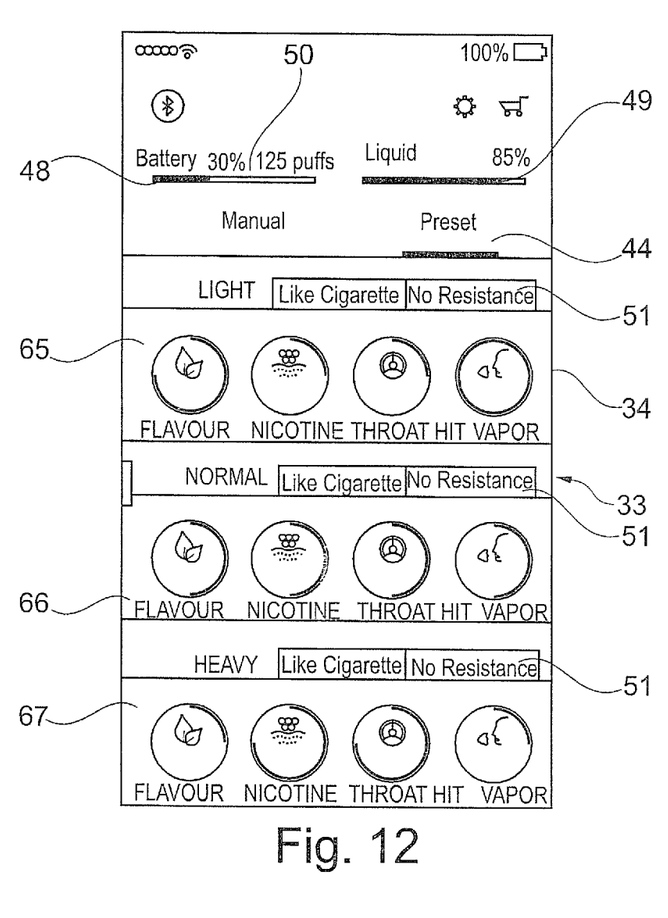

FIGS. 11 and 12 relate to the individual evaporation of two liquids A, B, for example by means of an evaporator device analogous to FIG. 2 having two carriers 2 and one evaporator 3 each (see FIGS. 8 and 9). For example, one of the liquid reservoirs 37A contains a liquid with flavour but without nicotine. The other liquid reservoir 37B contains nicotine but no flavour.

With the correspondingly presented inhaler 27 and the app, the consumer can adjust his smoking experience as much as possible by specifying a desired maximum amount of vapour.

The app advantageously includes the screen display shown in FIG. 11, which allows for a detailed and differentiated control or adjustment of the inhaler 27, and which can therefore be referred to as expert mode or manual mode. This mode can be called up by the consumer, for example, by pressing a corresponding button 35, which is designated "Manual" in FIGS. 11 and 12. If the manual screen display shown in FIG. 11 is displayed and the app is in the manual mode, this can be displayed graphically, here, for example, by a highlighted bar in the lower region of the button 35.

In the manual mode, each liquid A, B contained in the inhaler 27 can advantageously be controlled separately. For example, in FIG. 11 the intensity of the flavour from liquid A in the vapour/aerosol can be set between minimum ("soft", level 1) and maximum ("strong", level 5) by tapping the corresponding level in the level bar 36. In a similar manner, the intensity of the nicotine from liquid B in the vapour/aerosol can be set between minimum ("light", level 1) and maximum ("heavy", level 5) by tapping the corresponding level in the level bar 37.

Accordingly, the consumer can choose between a 100% nicotine experience (controller 36 at maximum), a 100% taste experience (controller 37 at maximum), or a mixture of both.

Another adjustment in manual mode can affect the so-called throat hit, i.e. a short-term effect in the throat of the consumer. The throat hit correlates with the nicotine and the total amount of propylene glycol in the vapour. The throat hit, i.e. the intensity of nicotine from liquid B and propylene glycol in the vapour/aerosol, can be adjusted in FIG. 11 in a targeted manner between minimum ("soft", level 1) and maximum ("strong", level 5) by tapping the corresponding level in the level bar 38.

Furthermore, in manual mode, the total amount of vapour can advantageously be adjusted between minimum ("little", level 1) and maximum ("plenty", level 5) by tapping the corresponding level in the level bar 39. The maximum amount of vapour corresponds to the simultaneous operation of all the (here both) evaporators 3 of the evaporation device 1. The adjusted amount of vapour thus advantageously results from the sum of the evaporation intensities of the individual liquids A and B.

Of course, instead of the level bars 35-38, alternatively sliding bars or any other suitable multi-step actuating elements can be provided.

The evaporation parameters that can be adjusted in the manual mode are interdependent. If, for example, the evaporation of the liquid B, and thus the nicotine content in the produced vapour/aerosol, is adjusted to zero with the adjustment element 37, the total amount of vapour in the present example can be at most half as large as with the maximum nicotine content adjusted because only the liquid A is evaporated with half of all the evaporators 3. The same applies if one of the two liquids A, B is exhausted.

The app takes into account all the interdependencies of the evaporation parameters and adjusts the screen displays accordingly. For example, in the above-mentioned example, if the amount of nicotine were reduced by means of the adjustment element 37, the adjustment element 39 for the amount of vapour would also be automatically and simultaneously reduced to a maximum of half the value.

The same applies to the preset mode according to FIG. 12. If, for example, the liquid B is exhausted, profiles that have a certain minimum nicotine content can no longer be selectable, for example.

The app advantageously also includes the screen display shown in FIG. 11, which allows simplified control or setting of the inhaler 27 and which can therefore be referred to as a simplified mode or preset mode. This mode can be called up, for example, by pressing a corresponding button 44, which is labelled "Preset" in FIGS. 11 and 12. If the manual screen display shown in FIG. 12 is displayed and the app is in preset mode, this can be displayed graphically, here, for example, by a highlighted bar in the lower region of the button 44.

In the simplified or preset mode, a plurality of, for example three, different, predefined evaporation profiles can advantageously be selected by the consumer. For example, three different profiles are shown in FIG. 12 light ("Light"), normal, and strong ("Heavy"). Each profile can be selected by the consumer using a corresponding button 65, 66, 67.

In FIG. 12, for example, the profile "normal" is selected, which is indicated by a highlight, here a highlighted bar to the left of the word "Normal". Each profile includes a preset level for the individual parameters shown in FIG. 11. For example, if the profile "normal" is preset in FIG. 12: Flavour A level 3; Nicotine B level 3; Throat hit level 3; Vapour quantity level 4. For example, if the profile "Heavy" is preset in FIG. 12: Flavour A level 2; Nicotine B level 4; Throat hit level 4; Vapour quantity level 2.

In view of the choice options that are limited to the essential, the consumer can adjust a desired smoking experience easily and without having to think much about it.

Additionally or alternatively, the inhaler 27 can have a switch 54, for example a slide switch, which is arranged on the housing and which likewise allows for a selection of evaporation profiles.

The app preferably includes an indicator 48 for the state of charge of the energy store 46 in the inhaler 27, for example as a percentage of the maximum state of charge, and/or as an indication of the puffs remaining to the consumer.

The app preferably includes an indicator 49 for the remaining amount of liquid in the reservoir (s) 37A, 37B, ... of the inhaler 27, for example as a percentage of the maximum amount of liquid. The indicator 49 relates here to the total amount of liquid in all the reservoirs 37A, 37B, .... However, the individual remaining amount of liquid in each individual reservoir 37A, 37B, ... can also be displayed.

The app can also advantageously have an indicator 50 for the puffs remaining to the consumer. The number of remaining puffs can be calculated depending on the selected settings, the smoking behaviour, for example the average individual puff lengths, and the energy requirement.

Finally, the app can have a switching element 51 for setting the puff resistance of the inhaler 27, by means of an element 52 in the inhaler 27 that changes the puff resistance (see FIG. 1). In the example of FIGS. 11 and 12, the switching element 51 can be used to set two different puff resistances, namely a puff resistance which corresponds to that of a conventional cigarette (left switch position "Like Cigarette") and the lowest possible puff resistance (right switch position "No Resistance"). It is possible to set three or more different puff resistances.

The indicators 48, 49, 50, and/or 51 can advantageously be shown on all the screen displays of the app.

Additionally or alternatively, the inhaler 27 can have a switch 55 arranged on the housing, for example a slide switch, which likewise allows a selection of different puff resistances of the inhaler 27 by actuating the element 52 that changes the puff resistance. The element 52 and the switch 55 can also be one and the same part.

The app can have a button (not shown) for triggering a boost, in addition or as an alternative to the mechanical boost switch 30 on the inhaler 27, for example.

The previously described combination of evaporators 3, carriers 2 and reservoirs 37A, 37B, ... allows a large variety of setting options and thus high added value for the consumer due to a high degree of customisation of the smoking experience in terms of vapour quantity and taste.

Figure 13:
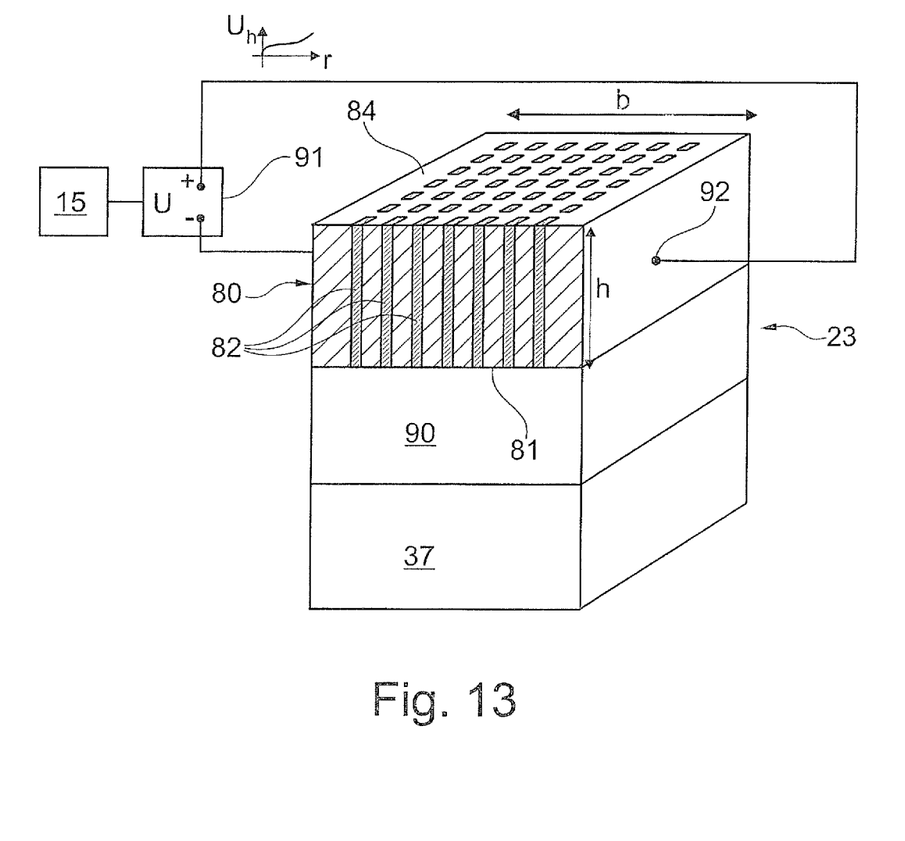
FIG. 13 is a schematic cross-sectional view of an exemplary evaporator unit for an e-cigarette.

An advantageous embodiment of an evaporator 3 according to the invention is shown in FIG. 13. The evaporator 3 is here formed by a block-shaped, advantageously monolithic heating element 80 or a volume heating element, preferably made of an electrically conductive material, preferably silicon, doped ceramic, metal ceramic, filter ceramic, semiconductor, particularly germanium, graphite, semimetal, and/or metal. It is not necessary for the entire heating element 80 to be made of an electrically conductive material. It may be sufficient, for example, that the surface of the heating body 80 is coated in an electrically conductive manner, for example has a metallic coating. In this case, the entire surface does not have to be coated; for example, conductor tracks can be provided on a non-conductive base body. Volume heaters allow a more compact design than spiral heaters, other wire heaters and/or filament heaters.

The heating element 80 is provided with a plurality of microchannels 82, which connect an inlet side 81 of the heating element 80 with an outlet side 84 in a liquid-conducting manner. The inlet side 81 is connected, for example, to the liquid store 37 in a liquid-conducting manner via a wick structure 90. The wick structure 90 is used for the passive conveyance of liquid from the liquid store 37 to the heating element 80 by means of capillary forces. The wick structure 90 in the contact region 81 to the radiator 80 serves to distribute liquid evenly, to be temperature-resistant and to form a kind of check valve with its relatively small pores and/or thin capillaries in order to prevent undesirable backflow of bubbly liquid from the heating element 80 into the wick structure 90 and/or into the liquid store 37.

Instead of the wick structure 90, other passive and/or active conveying devices for conveying liquid from the liquid store 37 to the heating element 80 can be provided.

The median diameter of the microchannels 82 is preferably in the range between 5 µm and 200 µm, more preferably in the range between 30 µm and 150 µm, even more preferably in the range between 50 µm and 100 µm. Due to these dimensions, a capillary effect is advantageously produced, so that liquid penetrating into a microchannel 82 at the inlet side 81 rises upwards through the microchannel 82 until the microchannel 82 is filled with liquid. The volume ratio of the microchannels 82 to the heating element 80, which can be referred to as the porosity of the heating element 80, is for example in the range between 10% and 50%, advantageously in the range between 15% and 40%, further advantageously in the range between 20% and 30%, and is, for example, 25%.

The edge lengths of the surfaces of the heating element 80 provided with microchannels 82, for example, are in the range between 0.5 mm and 3 mm. For example, the dimensions of the surfaces of the heating element 80 provided with microchannels 82 can be as follows: 0.95 mm×1.75 mm; 1.9 mm×1.75 mm or 1.9 mm×0.75 mm. The edge lengths of the heating element 80 can be, for example, in the range between 0.5 mm and 5 mm, preferably in the range between 0.75 mm and 4 mm, more preferably in the range between 1 mm and 3 mm. The surface of the heating element 80 (chip size), for example, can be 1 mm×3 mm or 2 mm×3 mm.

The width b of the heating element 80 is preferably in the range between 1 mm and 5 mm, more preferably in the range between 2 mm and 4 mm, and is, for example, 3 mm. The height h of the heating element 80 is preferably in the range between 0.05 mm and 1 mm, more preferably in the range between 0.1 mm and 0.75 mm, even more preferably in the range between 0.2 mm and 0.5 mm, and is, for example, 0.3 mm.

The number of microchannels 82 is preferably in the range between four and 1000. This allows the heat input from the carrier into the microchannels 82 to be optimised and ensures a high evaporation capacity and a sufficiently large vapour outlet surface.

The microchannels 82 are advantageously arranged in the form of a square, rectangular, polygonal, round, oval or differently shaped array. The array may be in the form of a matrix having s columns and z rows, wherein s is advantageously in the range between 2 and 50 and further advantageously in the range between 3 and 30 and/or z is advantageously in the range between 2 and 50 and further advantageously in the range between 3 and 30. This allows for an effective and easily manufactured arrangement of microchannels 82 having a guaranteed high evaporation capacity.

The cross section of the microchannels 82 can be square, rectangular, polygonal, round, oval or otherwise shaped and/or can vary lengthwise in portions, in particular may increase, decrease or remain constant.

The length of one or each microchannels 82 is preferably in the range between 100 µm and 1000 µm, more preferably in the range between 150 µm and 750 µm, even more preferably in the range between 180 µm and 500 µm, and is, for example, 300 µm. This allows an optimum liquid absorption and a portion formation with sufficient heat input from the heating element 80 into the microchannels 82.

The distance between two microchannels 82 is preferably at least 1.3 times the clear diameter of one microchannel 82, wherein the distance refers to the centre axes of the two microchannels 82. The distance can preferably be 1.5 to 5 times the clear diameter of a microchannel 82, more preferably 2 to 4 times. In this way, an optimal heat input from the carrier into the microchannels and a sufficiently stable arrangement and wall thickness of the microchannels can be realised.

The evaporator unit 20 has a heating voltage source 91, preferably controllable by the control device 56, which is connected via electrodes 92 to opposite sides of the heating element 80, in such a manner that an electrical voltage Uh produced by the heating voltage source 91 leads to a current flow through the heating element 80. Due to the ohmic resistance of the electrically conductive heating element 80, the current flow leads to heating of the heating element 80 and therefore to evaporation of the liquid contained in the microchannels 82. The heating element 80 thus acts as an evaporator 3.

The duration of the individual evaporation steps at different temperatures and/or an evaporation of the individual components of the individual portions of the liquid can be kept so short and/or clocked using an activation frequency that the step-by-step evaporation cannot be perceived by a consumer and nevertheless a largely homogeneous, repeatable, precise aerosol formation having good taste conformity can be ensured. In particular, it is advantageous to first evaporate a low-boiling component of the liquid in a first evaporation interval at a first temperature A, and then to evaporate a high-boiling component of the liquid in a second evaporation interval at a second temperature B, which exceeds temperature A.

The heating element 80 can advantageously be produced using thin-film layer technology from sections of a wafer having a customary layer thickness.

The evaporator 3 is set in such a manner that an advantageous quantity of liquid is added in the range between 1 µl and 20 µl, more preferably between 2 µl and 10 µl, even more preferably between 3 µl and 5 µl, typically 4 µl per puff by the consumer. The evaporators 3 can preferably be adjustable in terms of the amount of liquid per puff.

The evaporators 3 can advantageously be adjusted in such a way that predominantly liquid drops are created having a diameter in the range between 0.05 µm and 5 µm, preferably between 0.1 µm and 3 µm. Droplet sizes in the range between 0.05 and 5 MMAD (mass median aerodynamic diameter), preferably between 0.1 and 3 MMAD, more preferably between 0.5 and 2 MMAD, even more preferably between 0.7 and 1.5 MMAD, for example around 1 MMAD can be optimal. MMAD corresponds to an EU standard and is specified in µm.

The activation frequency of the heating element 80 produced by the heating voltage source 91 is generally advantageously in the range from 1 Hz to 50 kHz, preferably in the range from 30 Hz to 30 kHz, and even further advantageously in the range from 100 Hz to 25 kHz.

The course of the evaporation procedure is explained below.

In an initial state, the voltage source 91 for the heating procedure is switched off.

To evaporate liquid, the voltage source 91 for the heating element 80 is activated. The voltage Uh is set in such a manner that the evaporation temperature in the heating element 80 and therefore in the microchannels 82 is adapted to the individual evaporation behaviour of the liquid mixture used. This prevents the danger of local overheating and thereby the formation of harmful substances.

As soon as a quantity of liquid equal to or related to the volume of the microchannels 82 has evaporated, the heating voltage source 91 is deactivated. Since the liquid properties and amount are advantageously known exactly, this point in time can be controlled very precisely. The energy consumption of the evaporator 3 can therefore be reduced compared to known devices, since the required evaporation energy can be dosed and thereby introduced more precisely.

After completion of the heating procedure, the microchannels 82 are predominantly or completely emptied. The heating voltage 91 is then kept switched off until the microchannels 82 are replenished by feeding liquid through the wick structure 90. When this happens, the next heating cycle can be started by switching on the heating voltage 91.

The heating element 80 is preferably produced on the basis of MEMS technology, in particular from silicon, and is therefore advantageously a micro-electromechanical system.

EMBODIMENTS

Embodiment 1. Inhaler (27), particularly an electronic cigarette product, comprising at least one evaporator device (1) having at least one electrical evaporator (3) for evaporating liquid supplied to the evaporator (3), and an electronic control device (56) for controlling and/or regulating the evaporator (3), characterised in that the evaporator device (1) is associated or can be associated with a plurality of liquids, in such a way that the composition and/or the vapour production rate of the vapour/aerosol produced by the at least one evaporator can be adjusted and/or modified in a targeted manner, as the control device (56) is designed for the individual control of the at least one or each individual evaporator (3) and/or for group control of the evaporators (3).

Embodiment 2. Inhaler according to embodiment 1, characterised in that the evaporator device (1) has a plurality of liquid feeds (16) for supplying the plurality of liquids A, B, . . . to the at least one evaporator (3).

Embodiment 3. Inhaler according to either embodiment 1 or embodiment 2, characterised in that a plurality of parameter sets adapted to the plurality of liquids A, B, C are stored in the electronic control device (56).

Embodiment 4. Inhaler according to any of the preceding embodiments, characterised in that the evaporator device (1) has a plurality of evaporators (3).

Embodiment 5. Inhaler according to embodiment 4, characterised in that each liquid A, B, is assigned at least one separate evaporator (3).

Embodiment 6. Inhaler according to any of the preceding embodiments, characterised in that the inhaler (27) has a user interface (32) via which a user can influence the composition of the vapour/aerosol produced by the at least one evaporator (3).

Embodiment 7. Inhaler according to any of the preceding embodiments, characterised in that the user interface (32) is a wireless interface for communication with a mobile communication terminal (33) of the user, particularly a smartphone.

Embodiment 8. Inhaler according to any of the preceding embodiments, characterised in that the liquids A, B, . . . contain one or more components from the group 1,2-propylene glycol, glycerol, water, at least one active ingredient, particularly nicotine, and/or at least one flavouring agent (flavour).

Embodiment 9. Inhaler according to any of the preceding embodiments, characterised in that at least one of the liquids A, B, . . . contains more than 50% glycerol.

Embodiment 10. Inhaler according to any of the preceding embodiments, characterised in that at least one of the liquids A, B, . . . contains at least 1% nicotine and at least one of the liquids A, B, . . . contains no nicotine.

Embodiment 11. Inhaler according to any of embodiments 1 to 9, characterised in that each of the liquids A, B, . . . supplied to the at least one evaporator (3) is free of nicotine.

Embodiment 12. Inhaler according to any of the preceding embodiments, characterised in that at least one of the liquids A, B, . . . contains a flavour and at least one of the liquids A, B, . . . contains no flavour, or another flavour.

Embodiment 13. Inhaler according to any of the preceding embodiments, characterised in that the inhaler (27) has a plurality of reservoirs (37A, 37B, . . . ) for storing the plurality of liquids A, B, . . . .

Embodiment 14. Inhaler according to embodiment 13, characterised in that at least one of the liquids A, B, . . . mostly contains one or more components from the group 1,2-propylene glycol and another of the liquids A, B, . . . mostly contains glycerol.

Embodiment 15. Inhaler according to any of the preceding embodiments, characterised in that the inhaler (27) has at least one capsule for storing a solid containing a flavour and/or an active substance, particularly containing nicotine, wherein the vapour/aerosol produced by the at least one evaporator is able to flow through the capsule.

Embodiment 16. Computer program product, particularly an application software or app, for a mobile communication terminal (33), the computer program product being designed to control and/or adjust an inhaler (27) according to any of the preceding embodiments.

Embodiment 17. Computer program product according to embodiment 16, characterised in that the computer program product has selection elements (65, 66, 67) for selecting one of a plurality of preset evaporation profiles and for corresponding actuation of the inhaler (27).

Embodiment 18. Computer program product according to embodiment 17, characterised in that preset evaporation profiles are provided with at least two, preferably at least three different degrees of strength of active substance content and/or throat hit.

Embodiment 19. Computer program product according to any of embodiments 16 to 18, characterised in that the computer program product comprises adjustment elements (36-39, 51) for adjusting individual evaporation parameters of the inhaler (27).

Embodiment 20. Computer program product 19, characterised in that the computer program product comprises adjustment elements (36-39) for adjusting the proportion of individual liquids A, B . . . in the vapour/aerosol produced.

Embodiment 21. Computer program product according to either embodiment 13 or embodiment 19, characterised in that the computer program product comprises an adjustment element (38) for adjusting a throat hit.

Embodiment 22. Computer program product according to embodiment 19 to 21, characterised in that the computer program product comprises an adjustment element (36, 37) for adjusting the flavour and/or active ingredient content.

Embodiment 23. Computer program product according to any of embodiments 19 to 22, characterised in that the computer program product comprises an adjustment element (39) for adjusting the total amount of vapour produced.

Embodiment 24. Computer program product according to any of embodiments 19 to 23, characterised in that the selectability of the evaporation parameters is coupled to one another.

Embodiment 25. Computer program product according to any of embodiments 16 to 24, characterised in that an indicator (48) is provided for the state of charge of the energy store (46) in the inhaler (27).

Embodiment 26. Computer program product according to any of embodiments 16 to 25, characterised in that an indicator (49) is provided for the remaining amount of liquid in the reservoir(s) (37A, 37B, . . . ) of the inhaler (27).

Embodiment 27. Computer program product according to any of embodiments 16 to 26, characterised in that an indicator (50) is provided for the puffs remaining to the consumer.

Embodiment 28. Computer program product according to embodiment 27, characterised in that the number of remaining puffs is calculated depending on the selected settings, the smoking behaviour, for example the average individual puff lengths, and the energy requirement.

Embodiment 29. Computer program product according to any of embodiments 16 to 28, characterised in that a switching element (51) is provided for adjusting the puff resistance of the inhaler (27).

Embodiment 30. Computer program product according to embodiment 29, characterised in that the switching element (51) can be used to adjust a puff resistance corresponding to a conventional cigarette and/or the lowest possible puff resistance.

The invention claimed is:

1. An inhaler, comprising:
    at least one evaporator device having at least one electrical evaporator for evaporating liquid supplied to the at least one electrical evaporator;
    an electronic control device for controlling and/or regulating the at least one evaporator device,
    wherein the at least one evaporator device is associated with a plurality of liquids in such a way that a composition and/or the vapour production rate of vapour/aerosol produced by the at least one evaporator device is adjustable and/or modifiable in a targeted manner, as the electronic control device is configured for individual control of one or more of the at least one evaporator device,
    the at least one evaporator device comprises at least one carrier, wherein each carrier of the at least one carrier has at least one evaporator and a standardized interface for electrical contacting of the evaporator of the at least one evaporator,
    wherein the evaporator is formed by a block-shaped heating element made of an electrically conductive material, and
    wherein the block-shaped heating element is provided with a plurality of microchannels, wherein the plurality of microchannels connect an inlet side of the block-shaped heating element with an outlet side of the block-shaped heating element in a liquid-conducting manner.

2. The inhaler according to claim 1, wherein the at least one evaporator device has a plurality of liquid feeds for supplying the plurality of liquids to the at least one electrical evaporator.

3. The inhaler according to claim 1, wherein a plurality of parameter sets adapted to the plurality of liquids are stored in the electronic control device.

4. The inhaler according to claim 1, wherein the at least one evaporator device comprises a plurality of electrical evaporators.

5. The inhaler according to claim 4, wherein each liquid of the plurality of liquids is assigned a corresponding electrical evaporator of the plurality of electrical evaporators.

6. The inhaler according to claim 1 further comprising:
    a user interface via which a user can influence a composition of the vapour/aerosol produced by the at least one electrical evaporator.

7. The inhaler according to claim 6, wherein the user interface is a wireless interface for communication with a mobile communication terminal of the user.

8. The inhaler according to claim 1, wherein the plurality of liquids contain one or more components from the following group: 1,2-propylene glycol, glycerol, water, at least one active ingredient, nicotine, and at least one flavouring agent (flavour).

9. The inhaler according to claim 1, wherein at least one liquid of the plurality of liquids contains more than 50% glycerol.

10. The inhaler according to claim 1, wherein at least one liquid of the plurality of liquids contains at least 1% nicotine and at least one liquid of the plurality of liquids contains no nicotine.

11. The inhaler according to claim 1, wherein the plurality of liquids supplied to the at least one electrical evaporator is free of nicotine.

12. The inhaler according to claim 1, wherein at least one liquid of the plurality of liquids contains a flavour and at least one liquid of the plurality of liquids contains no flavour, or another flavour.

13. The inhaler according to claim 1, further comprising:
    a plurality of reservoirs for storing the plurality of liquids.

14. The inhaler according to claim 13, wherein at least one liquid of the plurality liquids mostly contains one or more components from the group 1,2-propylene glycol and another liquid of the plurality of liquids mostly contains glycerol.

15. The inhaler according to claim 1, further comprising:
    at least one capsule for storing a solid containing a flavour and/or an active substance, wherein vapour/aerosol produced by the at least one electrical evaporator is able to flow through the at least one capsule.

* * * * *